United States Patent [19]
Hani et al.

[11] Patent Number: 5,298,249
[45] Date of Patent: Mar. 29, 1994

[54] COMPOSITIONS COMPRISING N-HYDROXYQUINAZOLINONE AND 2-N-HYDROXYTHIOUREA BENZOATE COMPOUNDS AS BIOCIDES

[75] Inventors: Rahim Hani, Cheshire; Phillip T. Berkowitz, Woodbridge; John L. Peterson, Milford, all of Conn.

[73] Assignee: Olin Corporation, Cheshire, Conn.

[21] Appl. No.: 770,834

[22] Filed: Oct. 4, 1991

[51] Int. Cl.$^5$ ................ A01N 25/00; A01N 43/54; A01N 47/28; C07D 239/95
[52] U.S. Cl. .................... 424/405; 514/259; 514/587; 252/47.5; 252/106; 252/107; 106/18.33; 544/285; 564/26
[58] Field of Search ............ 514/259, 585, 587; 252/475, 106, 107, DIG. 13; 424/78.09, 405; 106/18.33; 544/285; 564/26

[56] References Cited
U.S. PATENT DOCUMENTS

4,521,420 6/1985 Maurer et al. .................. 514/259
4,753,943 6/1988 King et al. ...................... 514/259

OTHER PUBLICATIONS

Barton et al., "Radical Chemistry of Thiohydroxamic acid esters" Tetrahedron Letters (1983) 24 (52) pp. 5889–5892.
Barton et al., "On the Mechanism of the Decarboxylative . . ." Tetrahedron Letters (1985) 26 (48) pp. 5943–5946.
Capuano et al., "Cyclische Hydroxamsäuren und . . ." Chemische Berichte (1970) 103 pp. 82–89.
Chemical Abstracts 79 (1973) 137075d, Stoffel et al.
Stoffel, R. et al., Achiv der Pharmazie (Weinheim, Germany) 306 (8) (1973) 579–86.

Primary Examiner—Mukund J. Shah
Assistant Examiner—Matthew V. Grumbling
Attorney, Agent, or Firm—Dale L. Carlson

[57] ABSTRACT

The present invention relates to a composition comprising an antimicrobial effective amount of a biocide selected from the group consisting of aromatic 2-N-hydroxy-thiourea and N-hydroxy-quinazolinone, and derivatives and combinations thereof, and at least one component selected from the group consisting of soaps, shampoos, skin-care medicaments, cosmetics, plastics and paints. Also disclosed is a novel process for making the biocide.

1 Claim, No Drawings

COMPOSITIONS COMPRISING N-HYDROXYQUINAZOLINONE AND 2-N-HYDROXYTHIOUREA BENZOATE COMPOUNDS AS BIOCIDES

FIELD OF THE INVENTION

This invention relates to the use of 2-N-hydroxythiourea benzoate and hydroxyquinazolinone compounds as biocides, particularly uv stable fungicides. These biocides exhibit excellent antifungal activity and uv light stability.

BACKGROUND OF THE INVENTION

Compounds exhibiting excellent biocidal activity are well-known in the art. For example, pyrithione salts, such as zinc pyrithione, are known to provide excellent biocidal activity, including broad spectrum anti-bacterial and anti-fungal activity. There are many uses for these pyrithione biocides. By way of illustration, U.S. Pat. No. 4,818,436 discloses the use of pyrithiones in metalworking fluids; U.S. Pat. No. 4,401,770 discloses urethane shoe inserts having antimicrobial activity; and U.S. Pat. No. 4,935,061 discloses their use in paints.

Despite the excellent biocidal (particularly fungicidal) activity attributable to the pyrithione salts, these compounds do have drawbacks for certain applications, most notably poor ultraviolet ("uv") light stability. Accordingly, new compounds exhibiting excellent biocidal activity but also exhibiting enhanced uv light stability would be highly desired by the biocides manufacturing community.

SUMMARY OF THE INVENTION

In one aspect, the present invention relates to a composition comprising an antimicrobial effective amount of a biocide selected from the group consisting of 2-N-hydroxythiourea benzoate and N-hydroxy-quinazolinone, and derivatives and combinations thereof, and at least one component selected from the group consisting of soaps, shampoos, skin-care medicaments, cosmetics, metalworking fluids, plastics and paints.

In another aspect, the present invention relates to a process for producing a 2-N-hydroxythiourea benzoate compound which comprises:

(a) reacting a 2-nitrobenzoate(s) with a reducing agent (preferably a zinc reducing agent and preferably in the presence of ammonium chloride) in a solvent consisting essentially of water plus tetrahydrofuran at a reaction temperature of between about −10° C. and about 20° C. in order to reduce the 2-nitrobenzoate(s) to an aromatic hydroxylamine derivative thereof, and (b) reacting said aromatic hydroxylamine derivative with isothiocyanate to produce the 2-N-hydroxythiourea benzoate compound.

In yet another aspect, the present invention relates to a process for producing an N-hydroxy-quinazolinone compound which comprises the steps of:

(a) reacting a 2-nitrobenzoate(s) with a reducing agent (preferably a zinc reducing agent and preferably in the presence of ammonium chloride) and combinations thereof in a solvent consisting essentially of water plus tetrahydrofuran at a reaction temperature of between about −10° C. and about 20° C. in order to reduce the 2-nitrobenzoate(s) to an aromatic hydroxylamine derivative thereof, and (b) reacting said aromatic hydroxylamine derivative with isothiocyanate to produce the 2-N-hydroxythiourea benzoate compound, and (c) reacting said 2-N-hydroxythiourea benzoate compound with a base (preferably sodium hydroxide or triethanolamine) in a cyclization reaction to produce the N-hydroxyquinazolinone compound.

These and other aspects will become apparent upon reading the following detailed description of the invention.

DETAILED DESCRIPTION OF THE INVENTION

It has been surprisingly found in accordance with the present invention that certain N-hydroxy adducts, namely 2-N-hydroxy-thiourea benzoates and N-hydroxy-quinazolinones, are particularly effective as biocides exhibiting excellent uv light stability (e.g., stability against degradation caused by ultraviolet light). Preferred N-hydroxy adducts are shown by the empirical structural formulae given in Table I hereinbelow (refer to the structural formulae identified (I) and (II) of Table I) wherein R, $R_1$, $R_2$ and $R_3$ identified therein are the same or different moieties selected from the group consisting of linear, branched and cyclic hydrocarbons having between 1 to 10 carbon atoms, and wherein $R_1$ can additionally be a halogen.

The process for producing these biocides in accordance with the present invention as recited hereinabove is also novel. In the past, aromatic N-hydroxylamines were prepared by the reduction of aromatic nitro compounds in water using a zinc reducing agent in the presence of ammonium chloride. However, the prior art process typically produces low yields of the aromatic N-hydroxylamine of between 12% and 76%. In contrast, the process of the present invention, which employs low temperature and a two phase reduction reaction in water and tetrahydrofuran, produced nearly quantitative yield of the desired N-hydroxylamine derivative. In addition, the reaction of hydroxylaminobenzoate with isothiocyanate in hexane yielded the N-hydroxythiourea in 92–95% yield. The N-hydroxythiourea is then cyclized by sodium hydroxide to N-hydroxyquinazoline to provide an approximately 92–99% yield of product. In carrying out the processes of the present invention, steps (b) and (c) employ molar ratios of reactants that can vary over a wide range of, for example, between about 1:10 and about 10:1. Preferably, a sufficient amount of the isothiocyanate is employed in step (b) and a sufficient amount of base is employed in step (c) to provide at least a slight molar excess of these reactants, relative to the aromatic hydroxylamine derivative and 2-N-hyrdroxythiourea benzoate, respectively.

The compounds employed as biocides in the present invention are used in an antimicrobial effective amount in the compositions of the present invention. By the term "antimicrobial effective amount" is meant an amount sufficient to impart to the compositions resistance against microbial attack by fungii and/or bacteria. Preferably the biocidal compounds are employed in the composition in an amount of between about 0.01 and about 10 weight percent, more preferably between about 0.01 and about 5 weight percent, based upon the total weight of the composition.

The reaction temperature utilized in step (a) of the process of the present invention is preferably below 20° C., more preferably below 15° C., most preferably between 0° C. and 10° C. Temperatures above 20° C. tend to cause formation of the diamino derivatives instead of the desired N-hydroxyamino derivatives.

The biocidal compounds preferred for use in accordance with the present invention include the following:
1-hydroxy-3-methyl-2-thioxo-1,2-dihydroquinazoline-4(3H)-one and the sodium salt thereof,
1-acetoyloxy-3-methyl-2-thioxo-1,2-dihydroquinazoline-4(3H)-one, as well as the compounds identified as IIj and III in Table I. A particularly preferred use for the biocidal compounds of the present invention is in Paints and paint bases (i.e., the paint before pigment addition).

Although the improved biocidal efficacy and gellation resistance advantages associated with the present invention are expected to provide advantages when used in a wide variety of paints, including indoor and outdoor household paints, industrial and commercial paints, particularly advantageous results are obtained when the process and composition of the present invention are utilized in conjunction with marine paints for use, for example, on ship's hulls. In addition, the composition and process of the present invention provides highly desirable results in the context of exterior paints of both the latex and alkyd types.

Typically, a paint composition will contain a resin, a pigment, and various optional additives such as thickening agent(s), wetting agents, and the like, as is well-known in the art. The resin is preferably selected from the group consisting of vinyl, alkyd, epoxy, acrylic, polyurethane and polyester resins, and combinations thereof. The resin is preferably employed in an amount of between about 20% and about 80% based upon the weight of the paint or paint base.

In addition, the paint composition of the present invention contains optional additional additives which have a favorable influence on the viscosity, the wetting power and the dispersibility, as well as on the stability to freezing and electrolytes and on the foaming properties. If a marine paint is being fabricated, the paint preferably contains a swelling agent to cause the paint to gradually "slough off" in its marine environment, thereby causing renewed biocidal efficacy of newly exposed biocide at the surface of the paint in contact with the water medium of the marine environment. Illustrative swelling agents are naturally-occurring or synthetic clays, such as kaolin, montomorillonite bentonite), clay mica (muscovite), and chlorite (hectonite), and the like. In addition to clays, other swelling agents, including natural or synthetic polymers, such as that commercially available as POLYMERGEL, have been found to be useful in the compositions of the present invention to provide the desired "sloughing off" effect. Swelling agents can be used singly or in combination. The total amount of optional additives is preferably no greater than 20% by weight, more preferably between about 1% and about 5% by weight, based upon the total weight of the paint composition.

Illustrative thickening agents include cellulose derivatives, for example methyl, hydroxyethyl, hydroxypropyl and carboxymethyl cellulose, poly(vinyl alcohol), poly (vinylpyrolidone), poly(ethylene-glycol), salts of poly(acrylic acid) and salts of acrylic acid/acrylamide copolymers.

Suitable wetting and dispersing agents include sodium polyphosphate, salts of low-molecular-weight poly(acrylic acid), salts of poly(ethane-sulfonic acid), salts of poly (vinyl-phosphonic acid), salts of poly(- maleic acid) and salts of copolymers of maleic acid with ethylene, 1-olefins with 3 to 18 carbon atoms and/or styrene.

In order to increase the stability to freezing and electrolytes there may be added to the paint composition various monomer 1,2-diols, for example glycol, propylene-glycol-(1,2), and butylene-glycol-(1,2) or polymers thereof, or ethoxylated compounds, for example reaction products of ethylene oxide with long-chain alkanols, amines, carboxylic acids, carboxylic acid amides, alkyd phenols, poly(propylene-glycol) or poly(butylene-glycol).

The minimum temperature of film formation (white point) of the paint composition may be reduced by adding solvents, such as ethylene-glycol, butyl-glycol, ethyl-glycol acetate, ethyl-diglycol acetate, butyl-diglycol acetate, benzene or alkylated aromatic hydrocarbons. As defoaming agents there are suitable for example poly(propylene-glycol) and polysiloxanes.

The antimicrobial compounds of the present invention have many desirable properties. They exhibit excellent antimicrobial activity, show remarkable light stability and are compatible with chemicals used in metal-working fluids, personal care products, paints and polymers.

The paint composition of the present invention may be used as a paint for natural or synthetic materials, for example wood, paper, metals, textiles and plastics. It is particularly suitable as an outdoor paint, and is excellent for use as a marine paint.

Table I below provides a tabular listing of the compounds prepared in accordance with the working examples which follow. The acyl derivatives of (IIa) were also prepared via the reaction of (IIa) with acyl chlorides. These derivatives showed good microbial activity which demonstrates that substitution on the hydroxyl group does not adversely affect the antimicrobial activity of N-hydroxyquinazoline.

TABLE I

| Descriptions of compounds Ia-If, IIa, and IIc-IIn. | | | | |
|---|---|---|---|---|
| Compound | R | $R_1$ | $R_2$ | $R_3$ |
| Ia | Me | H | Me | |
| Ib | Et | H | Me | |
| Ic | Me | 4-Cl | Me | |
| Id | Me | 5-Me | Me | |
| Ie | Et | H | Ph | |
| If | Et | H | Allyl | |
| IIa | | H | Me | OH |
| IIc | | 7-Cl | Me | OH |
| IId | | 6-Me | Me | OH |
| IIe | | H | Ph | OH |
| IIf | | H | Allyl | OH |
| IIg | | H | H | OH |
| IIh | | H | Me | $CH_3O$ |
| IIi | | H | Me | $CH_3COO$ |
| IIj | | H | Me | $CH_2$=$CHCOO$ |
| IIk | | H | Me | PhCOO |
| III | | H | Me | $CH_2$=$CCH_3COO$ |
| IIm | | H | Me | HOCOO |
| IIn | | H | Me | $CH_3NHCOO$ | wherein "Me" denotes methyl and "Ph" denotes phenyl.

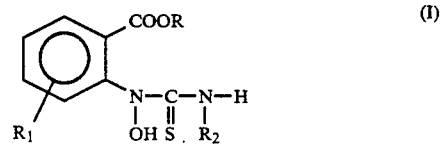

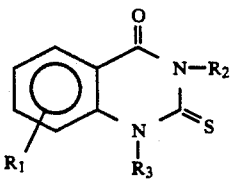

The following examples are intended to illustrate, but in no way limit, the scope of the present invention.

EXAMPLE 1

Preparation of 1-Hydroxy-3-Methyl-2-Thioxo-1,2-Dihydroquinazoline-4(3H)-ONE (IIa)

The preparation of compound IIa consisted of three steps: A) reduction of methyl or ethyl o-nitrobenzoate to methyl or ethyl 2-N-hydroxylamino benzoate, B) preparation of N-hydroxythiourea Ia from the reaction of methyl or ethyl 2-N-hydroxylaminobenzoate with isothiocyanate, and C) cyclization of Ia to N-hydroxyquinazolinone. The preparation of compounds Ia and IIa will serve to illustrate the general procedure for preparation of compounds Ib–If and IIc–IIf.

A. Preparation of Methyl,2-N-Hydroxylamino Benzoate

A 2 liter three-flask equipped with a thermometer and a mechanical stirrer was charged with 100.5 g (0.55 mole) of methyl 2-nitrobenzoate, 900 ml water, 760 ml tetrahydrofuran and 74.9 g (1.4 mole) of ammonium chloride. The mixture was cooled to 0° C. with constant stirring. To the mixture was added 90 g (1.3 mole) of powdered zinc in small increments during a two hour Period. Then the cold mixture was filtered. To the filtrate was added 80 g of sodium chloride and the organic layer was separated. The tetrahydrofuran was removed under reduced pressure, and the methyl 2-N-Hydroxylaminobenzoate was dried under reduced pressure overnight to yield an oily viscous material.

B. Preparation of Methyl, 2-[N¹-Hydroxy-N³-Methylthiouredio]-Benzoate (Ia)

To the methyl 2-N-Hydroxylamino benzoate from step A was added 350 ml of hexane and 43.97 g (0.6 mole) of methylisothiocyanate in 275 ml of hexane during 45 minutes period with constant stirring. The mixture was stirred at room-temperature for 2.5 hrs. The precipitate was filtered and dried to yield 113.2 g of N-hydroxythiourea Ia.

C. Preparation of 1-Hydroxy-3-Methyl-2-Thioxo-1,2-Dihydroquinazoline-4(3H)-ONE (IIa)

A 2l beaker was charged with 68.9 g (0.29 mole) of N-hydroxythiourea Ia, 845 ml of water and equipped with a mechanical stirrer. To the mixture was added a solution of 14.5 g (0.36 mole) of sodium hydroxide in 640 ml of water over 15 minutes. The mixture was heated to 75° C. and held for 1 hr., then filtered hot and cooled to room temperature. The pH was adjusted to 4.5 and the temperature reduced to 10° C. The product was filtered, washed with cold water and dried at 50° C. under vacuum overnight to yield 54.7 g (92%) of IIa. The cyclization of compounds Ic and Id to the compounds IIc and IId was done with triethylamine in the place of sodium hydroxide in a similiar manner.

EXAMPLE 2

Preparation of Compound IIg

Compound IIg was prepared in a similiar manner to IIa exept isothiocyanic acid was used instead of methylisothiocyanate.

EXAMPLE 3

Preparation of 1-Methyloxy-3-Methyl-2-Thioxo-1,2-Dihydroquinazoline-4(3H)-ONE (IIh)

To 0.98 g of IIa-Na in 79 ml of methanol was added 1.69 g of iodomethane and the reaction mixture refluxed for 1.5 hrs. The solution was cooled to room-temperature and the white precipitate filtered and dried under reduced pressure to give 0.4 g (yield 42.3%) of compound IIh with a melting point of 183.5°–184° C.

EXAMPLE 4

Preparation of 1-Acetoyloxy-3-Methyl-2-Thioxo-1,2-Dihydroquinazoline-4(3H)-ONE (IIi)

A slurry of 6.00 g (0.0260 mole) of 1-hydroxy-3-methyl-2- thioxo-1,2-dihydroquinazoline 4(3H)-one, sodium salt (IIa-Na) in 48 ml of methylene chloride was added to 2.1 g (0.0265 mole) of acetyl chloride at reflux. After 5 minutes, the colorless solution developed a white precipitate. After 1 hour at reflux, the reaction was cooled, filtered and the solvent was removed in vacuo to give 6.50 g of the crude product. The product was then recrystallized from 55 ml of methylene chloride and 150 ml of petroleum ether to give 4.62 g of compound IIi. The yield was 94.6%. Compound IIj–IIl were made in a similiar manner to compound IIi by using the appropriate acid chlorides and compound IIa-Na.

EXAMPLE 5

Preparation of 1-Carbonic Acid-3-Methyl-2-Thioxo-1,2-Dihydroquinazoline-4(3H)-ONE (IIm)

To 1.04 g (0.005 mol) of compound IIa in 20 ml of toluene at 9° C. was added 0.008 mol of phosgene. The reaction mixture was stirred at room- temperature for 1.5 hrs and 10 ml of water was added to the mixture and stirred 3.5 hrs. The organic layer was separated and solvent removed under vacuum to yield 0.95 g of compound IIm with a melting point of 128°–129° C.

EXAMPLE 6

Preparation of 1-N-Methylcarbamate-3-Methyl-2-Thio-1,2-Dihydroquinazoline-4(3H)-ONE (IIn)

To a 100 ml flask was added 3.0 g (0.014 moles) 1-hydroxy-3-methyl-2-thioxo-1,2-dihydroquinazoline-4(3H)-one (IIa) and 50 ml of dry tetrahydrofuran. Compound IIa dissolved in the solvent with mixing. By pipette was added 0.82 g (0.014 moles) methyl isocyanate. The flask was stoppered and mixing continued. Within 10 minutes a white precipitate had formed in the previously clear solution. The reaction was mixed at room temperature overnight. The product, compound IIn, was filtered out, washed with tetrahydrofuran and dried under vacuum to give 1.42 g (yield 37.2%) with a melting point of 167° C.

EXAMPLE 7

Preparation of Salts IIa-Na and IIa-Zn

The sodium or zinc salts of the compound IIa were prepared by reaction of IIa with sodium hydroxide or zinc sulfate in aqueous solution respectively.

EXAMPLE 8

Photochemistry of 1-Hydroxy-3-Methyl-2-Thioxo-1,2-Dihydroquinazoline-4(3H)-ONE (IIa)

The UV stability of IIa was evaluated using a immersion well photochemical apparatus equipped with a Hanovia 450 Watt medium pressure lamp. An aqueous solution (100 ppm in $KH_2PO_4$ buffer, pH=7) was irradiated at 25° C. with air agitation for a period of 110 minutes. The rate of photolysis was monitored by UV spectroscopy. Aliquots were taken through a side port of the apparatus into an amber vial and the absorption at 325 nm was measured. A sodium pyrithione aqueous solution (i.e., sodium OMADINE ® biocide) was irradiated similarly for comparative purposes.

Compound IIa exhibited a first order photodecomposition with a $T_{\frac{1}{2}}=55$ min which was considered excellent. In contrast, sodium pyrithione biocide decomposed in 15 seconds under the same conditions.

EXAMPLE 9

Determination of the Minimum Inhibitory Concentrations (MIC's) for Antimicrobial Compounds of this Invention Solutions of the experimental compounds in dimethyl sulfoxide and an aqueous solution of sodium pyrithione were serially diluted in nutrient broth (Tryptic Soy Broth for bacteria and Sabouraud Dextrose Broth for fungi) in microtiter plates. Equal volumes of a broth suspension of bacteria ($10^6$ CFU/ml) or fungi ($10^5$ cells or spores/ml) were added to each dilution, and the plates were incubated at 37° C. (bacteria and yeast) or 28° C. (molds). Bacteria, yeast, and molds were incubated two, five, and seven days respectively before determining the highest inhibitory dilution. The compounds showed less activity against bacteria than sodium pyrithione, but greater activity against fungi. N-hydroxyquinazolinone and its acylated derivative were five to forty-three times as active per molecule against three of the four fungi as sodium pyrithione. The data is presented in Table II which follows.

TABLE II

| Compounds | MIC (ppm) MIC of the N-hydroxythiourea and quinazoline derivatives. | | | |
|---|---|---|---|---|
| | A | B | C | D |
| Ib | 8 | 8 | 8 | 128 |
| Ic | <2 | 4 | 8 | 128 |
| Id | 8 | 8 | 8 | 512 |
| Ie | 16 | 32 | 64 | 64 |
| If | 4 | 16 | 16 | 16 |
| IIa | <2 | <2 | <2 | 128 |
| IIc | <2 | <2 | 4 | 64 |
| IId | <2 | 4 | <2 | 128 |
| IIe | 16 | 16 | 32 | 64 |
| IIf | 4 | 16 | 16 | 8 |
| IIg | 64 | 128 | 1024 | 512 |
| IIh | 256 | 512 | 512 | 512 |
| IIi | 2 | nt | nt | nt |
| IIj | 4 | 4 | 8 | 16 |
| IIk | 512 | 256 | 512 | 512 |
| IIl | 128 | 4 | 32 | 512 |
| IIm | 4 | 8 | 8 | 16 |
| IIn | 4 | 8 | 8 | 16 |
| IIa-Na | <2 | <2 | <2 | 4 |
| IIa-Zn | 32 | 128 | 512 | 512 |
| Na Pyrithione | — | — | — | — |

A = *Candida albicans*
B = *Aureobasidium pullulans*
C = *Aspergillus niger*
D = *Fusarium*
"nt" denotes not tested.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A paint composition comprising a resin, a pigment and a biocide, said resin being selected from the group consisting of vinyl, alkyl, epoxy, acrylic, polyurethane and polyester resins, and combinations thereof, and said biocide being present in an antimicrobial effective amount and being selected from the group consisting of 2-N-hydroxythiourea benzoates and 1-hydroxy-2-thioquinazolinones selected from the group consisting of 1-hydroxy-3-methyl-2-thio-1,2-dihydroquinazoline-4(3H)-one and sodium salts and zinc salts thereof, methyl 2-[$N^1$-hydroxy-$N^3$-methylthiouredio]-benzoate, 1-methyloxy-3-methyl-2-thioxo-1,2-dihydroquinazoline-4(3H)-one, 1-acetoyloxy-3-methyl-2-thioxo-1,2-dihydroquinazoline-4(3H)-one, 1-carbonic acid-3-methyl-2-thioxo-1,2-dihydroquinazoline-4(3H)-one, 1-N-methylcarbamate-3-methyl-2-thio-1,2-dihydroquinazoline-4(3H)-one, and combinations thereof.

* * * * *